(12) United States Patent
Snodgrass

(10) Patent No.: US 8,264,343 B2
(45) Date of Patent: Sep. 11, 2012

(54) WIRELESS COMMUNICATION FOR HYGIENE DISPENSER SYSTEMS

(75) Inventor: David L. Snodgrass, Stuart, FL (US)

(73) Assignee: Ultraclenz, LLC, Jupiter, FL (US)

( * ) Notice: Subject to any disclaimer, the term of this patent is extended or adjusted under 35 U.S.C. 154(b) by 331 days.

(21) Appl. No.: 12/560,250

(22) Filed: Sep. 15, 2009

(65) Prior Publication Data

US 2011/0063106 A1    Mar. 17, 2011

(51) Int. Cl.
*G08B 1/08* (2006.01)
(52) U.S. Cl. .................. 340/539.16
(58) Field of Classification Search ............ 340/539.16, 340/573.1, 539.12, 286.02, 13.24; 700/231
See application file for complete search history.

(56) References Cited

U.S. PATENT DOCUMENTS

| | | | |
|---|---|---|---|
| 7,015,816 B2* | 3/2006 | Wildman et al. | 340/573.1 |
| 7,423,533 B1* | 9/2008 | LeBlond et al. | 340/572.1 |
| 7,783,380 B2* | 8/2010 | York et al. | 700/240 |
| 7,830,852 B2* | 11/2010 | Twitchell, Jr. | 370/338 |
| 7,978,050 B2* | 7/2011 | Moshfeghi | 340/10.2 |
| 8,066,217 B2* | 11/2011 | Cittadino et al. | 242/563 |
| 2009/0273477 A1* | 11/2009 | Barnhill | 340/573.1 |

* cited by examiner

*Primary Examiner* — Phung Nguyen
(74) *Attorney, Agent, or Firm* — Lucas & Mercanti, LLP; Peter J. Phillips

(57) ABSTRACT

A communication system for handwash compliance monitoring, comprises a plurality of handwash monitoring sensors for collecting handwash compliance data at a respective plurality of handwash stations, at least one hub which wirelessly receives handwash compliance data transmitted from said plurality of handwash monitoring stations, a gateway which wirelessly receives handwash compliance data transmitted from the hub, and a wireless cellular telephone link for transmitting the handwash compliance data from the gateway to a central monitoring station.

22 Claims, 1 Drawing Sheet

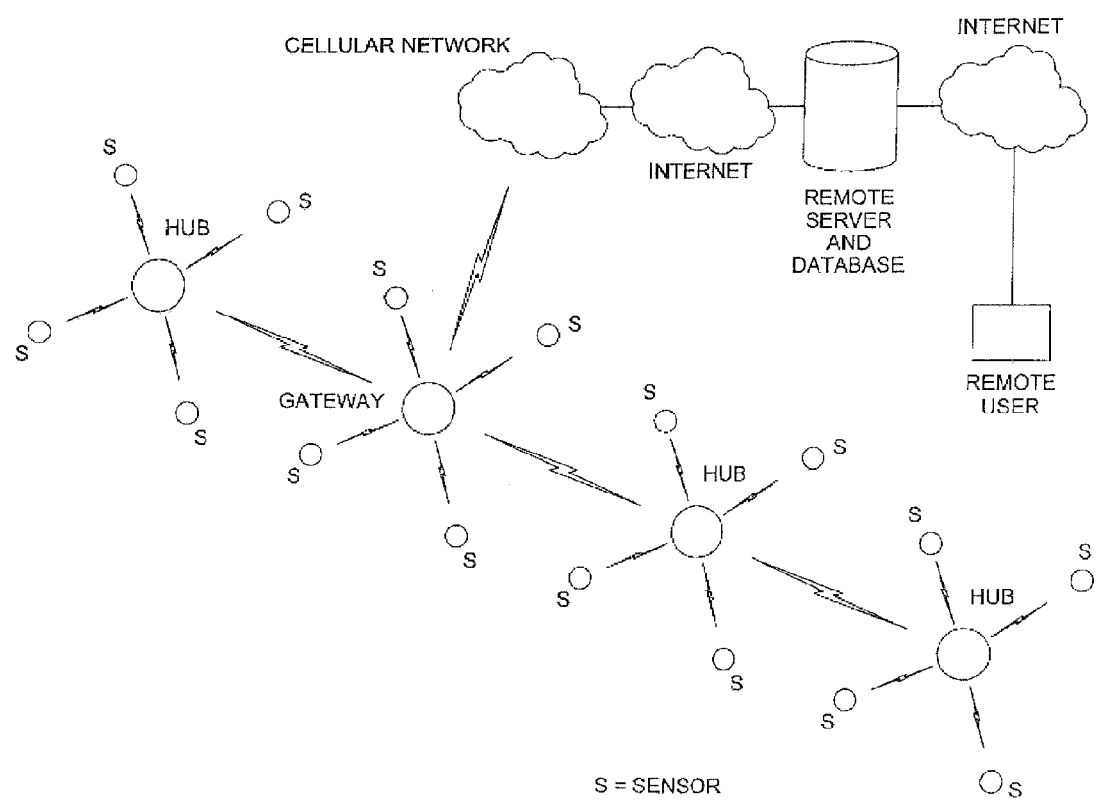

WIRELESS COMMUNICATION FOR HYGIENE DISPENSER SYSTEMS

BACKGROUND OF THE INVENTION

The present invention relates to handwash dispenser systems and for monitoring handwash compliance data by users of such systems, and more particularly to a communication system for wirelessly transmitting handwash compliance data from the dispensers to a central station, including a cellular telephone network.

Handwash compliance systems collect handwash compliance data collected by sensors at a handwash dispenser system. The data is typically stored locally at the handwash dispenser. The data may be transmitted over a communications line which may be a hard-wire, such as a half-duplex RS-485 network to a central location, which may receive data from a plurality of handwash dispenser. The data may be analyzed at the central location, and handwash compliance reports may be generated with a view towards insuring compliance with handwash protocols and regulations, and to improve compliance when compliance has been found to be lacking, not optimal, or in need of improvement in some way.

SUMMARY OF THE INVENTION

In some compliance systems, the handwash monitoring data is transferred over a local network at a customer site to a monitoring station which collects and analyses the information.

Sometimes a different entity, other than the customer, collects and analyzes the data, but the data is still transferred over the customer-owned or -operated network. This may result in security issues, as the different entity doing the monitoring, should not, from the customer's perspective, have access to the entire network which includes data other than handwash monitoring data. Also, the different entity doing the monitoring may be monitoring with a proprietary data protocol or other proprietary software application, which the different entity wishes to keep confidential from the customer.

If data is communicated over a data cable between the dispensers and a data collection device, the data cable may be expensive to install, especially for retro-fit applications. If the data collection device is a personal computer ("PC") which runs a proprietary application program at a different entity, both the customer and different entity can develop a strained relationship. If the customer opens a port in the customer's network firewall, security concerns are raised, subjecting the customer to possible security breaches by not only the different entity, but from other entities as well, seeking to hack into the customer's system through the firewall.

The present invention provides a communication arrangement which addresses some, or all, of the above concerns about cost, retro-fitting, security, and maintaining good relationships between the customer and different entity performing the data collection and compliance monitoring.

The present invention provides a reliable and cost-effective, low band-width wireless network that can be easily installed either initially, or retro-fitted in an indoor environment, and that is capable of communicating hand-wash monitoring data to an off-site location, while also minimizing the burden on the customer and the customer's personnel, and existing on-site customer's network infrastructure.

BRIEF DESCRIPTION OF THE DRAWING

FIG. 1 is a schematic diagram showing an overall configuration of sensors, hubs, a gateway, and a cellular network.

DESCRIPTION OF THE PREFERRED EMBODIMENT

A preferred embodiment according to the invention will be described, but the invention is not limited to this embodiment.

FIG. 1 is a schematic diagram showing an overall configuration of a communication system for handwash compliance monitoring according to the invention. The system 10 comprises a plurality of sensors S. Each sensor S collects handwash compliance data of a handwash fixture, such as a sink with a dispenser which dispenses hygiene product either manually or automatically (or both) as requested, or in response to, a user's presence. Examples of sensors are disclosed in U.S. Patent Application Publications 2006/0273361 and 2006/0273915, which are incorporated herein by reference. Briefly, a sensor will collect and store handwash compliance data, such as the identity of persons, at what times in the day such persons have performed a handwash procedure, and whether such handwash procedure has been correctly performed correctly according to a hygiene protocol. Variations of such compliance data may occur as understood by those skilled in the art.

The sensors may be embedded in the dispensers and may detect, and then transmit, or broadcast, data representing each dispenser activation and handwash compliance event. Hubs H, located within reception range of a plurality of sensors, will receive the transmitted data and re-transmit the data to a gateway G, servicing a plurality of hubs H. The gateway G will then transmit the data over a cellular network CN to a remote server RS with database store. The remote server RS can be connected to the internet, and remote users RU can log onto the remote server RS with appropriate password over the internet, and retrieve the remote dispenser activation event data for processing and analysis, such as generating hygiene compliance reports.

The transmission range of the sensors S may be on the order of 50 feet, or more, to ensure that respective hub H can receive the transmitted data. The transmission of the hub H will preferably have a longer range of 100 feet or more to ensure that the gateway G will receive the transmitted data from the hubs H.

The above-described topology will provide a network at good-performance and low-cost, avoiding hand-wiring of both original and retro-fit installations.

Hubs H can be located throughout a customer facility. In addition to receiving data from sensors S, and transmitting to a gateway G, the hubs H can also, or alternatively, function as repeaters, relaying data from one hub to another to the gateway G. Good radio frequency (RF) coverage will thus be obtained, while allowing the sensors to operate at low-power levels, thereby extending battery life. By having the hubs H, which are less costly than a gateway G, serve as repeaters, savings can result by having only one gateway G at a facility, although it may be useful to have a plurality of gateways G for redundancy in case of a failure of a gateway G. Hubs H can also be provided with ranges in an over-lapping manner, so that even if a hub H becomes inoperative or loses power, the remaining hubs H can provide the transmission and repeating operations.

The gateway G uses a cellular modem to transmit the data over a cellular network. As cellular modems are relatively costly to acquire and operate, minimizing the cellular modem count to a low number, even one, will minimize installation and operating costs.

The sensor S and hubs H may operate on 900 MHz or 2.4 GHz bands, but preferably will operate at 433 MHz to avoid interference with the former two bands which are popular and crowded. Also, the 433 MHz band is better able to penetrate obstacles, like walls. As other less crowded frequency bands become available, they may be used as well. Spread spectrum transmission may be used to reduce noise and/or interference.

Each sensor S is preferably self-powered with a battery so that it can be used with existing manual and touch-free dispensers, which do not presently have power available to power the sensor. The sensor S, especially for a manual dispenser, may have a mechanical interface such as a contact closure, magnetic reed switch, or Hall-effect sensor. The preferred interface is the contact closure as this is the most reliable.

The dispensers preferably have an "expansion port". The expansion port may have an active low 3.3V logic level pin available with a 100KΩ pull-up resistor. This pin goes active during the dispenser pump cycle which is about one second in duration. However, the manual dispenser's activation could be much shorter. To make the sensor compatible with both the manual and touch-free dispensers, the 100KΩ pull-up resistor may be removed from the touch-free dispenser. The sensor will have a 100KΩ pull-up resistor which makes the contact closure interface self contained and eliminates the need to add a pull-up resistor and Vcc source to the manual dispenser.

The manual dispenser is different from the touch-free because it is completely under user control. The sensor should be able to detect an activation event with a minimum duration of 100 ms. A user may not fully depress the push bar or push it very quickly causing the limit switch (contact closure) to only be closed for a short period of time. The sensor may be designed to detect up to 100 consecutive activation events in rapid succession. It is not uncommon for users to take multiple doses very rapidly. The sensor should be able to buffer up to 100 consecutive activation events in rapid succession also buffering a time offset, for each activation, based on the first activation in a rapid succession series (see Table 1). Buffering will also be preferred if one or more activations occur while the sensor is transmitting. The time offset will allow the hub to recognize the buffered activations as valid. The time offset can be added, by the hub, to the time stamp of the first activation thus resolving the time of activation for the buffered event. The time stamp will have a resolution of 1 second so it is possible that more than one valid activation will have the same time stamp. When the buffer is empty, the time offset will be cleared to 0.

Some sensors may be within range of more than one hub. This will result in multiple hubs collecting activation event data from one sensor. The remote server can detect and discard duplicate activation events before storing them in a database. More than one activation can have the same time stamp from the same sensor. To allow the server to distinguish between valid activations with the same time stamp and duplicate activations with the same time stamp, an 8-bit counter (see table 1) can be incremented with each activation. If the server sees two activations with the same time stamp from the same sensor but different counts, both activations are valid, otherwise one is a duplicate and can be discarded.

Multiple hubs may not have perfectly synchronized real-time clocks (RTC). In the case where two or more of these out of sync hubs are within range of a single sensor, each may record and time stamp the same activation event but the time stamps will not match. This creates a situation that makes it difficult for the remote server to detect duplicate activations unless an 8-bit activation count is implemented by the sensor.

TABLE 1

Possible Rapid Successive Activation Scenario

| Activation Event | | Time | Time Offset | 8-Bit Counter | Time Stamp |
|---|---|---|---|---|---|
| 1 | | 02:42:15.0 | 0 ms | 253 | 02:42:15 |
| 2 | | 02:42:15.1 | 100 ms | 254 | 02:42:15 |
| 3 | 1 | 02:42:15.6 | 600 ms | 255 | 02:42:15 |
| 4 | 2 | 02:42:16.1 | 1,100 ms | 0 | 02:42:16 |
| | | No Activity | | | |
| 1 | | 02:55:38.5 | 0 ms | 1 | 02:55:38 |

TABLE 1-continued

Possible Rapid Successive Activation Scenario

| Activation Event | | Time | Time Offset | 8-Bit Counter | Time Stamp |
|---|---|---|---|---|---|
| | | No Activity | | | |
| 1 | | 02:56:03.7 | 0 ms | 2 | 02:56:03 |
| | | No Activity | | | |
| 1 | | 03:11:26.4 | 0 ms | 3 | 03:11:26 |
| 2 | 2 | 03:11:26.8 | 400 ms | 4 | 03:11:26 |

The sensor will create an 8-byte event record for each activation that occurs (see Table 2). This record will be transmitted to the nearest hub. The event record will contain a factory programmed 32-bit device address that is unique to the sensor, an 8-bit device ID that will distinguish the current sensor from other sensors designed in the future, an 8-bit event ID to identify what kind of event occurred, an 8-bit activation count to identify duplicate event records and an 8-bit time offset to resolve activation time for multiple events occurring before they can be transmitted.

TABLE 2

8-Byte Sensor Event Record

| Device ID | Address Byte 0 | Address Byte 1 | Address Byte 2 | Address Byte 3 | Event ID | 8-Bit Activation Count | Time Offset |
|---|---|---|---|---|---|---|---|

The Address Bytes 0-3 may have a factory-programmed value between 0 and 4,294,967,296 that is unique for each sensor The Device ID may have a value from 0 to 255 that identifies the type of sensor from which the event record originated. The value for the current sensor (type 1) will be 0.

The Event ID may have a value from 0 to 255 that identifies the type of event that occurred. The current sensor (type 1) only has one event, a contact closure (dispenser activation). Sensors may have more event options such as cover open, cover closed, low battery, object blocking dispenser's IR etc. The value for a dispenser activation event will be 0.

The 8-Bit Activation Count may have a value between 0 and 255 that is incremented with each activation event. Consecutive activation events should not have the same number. When the count reaches 255, it will circle back to 0 on the following activation.

The Time Offset may have a value from 0 to 255 that, for the current activation, represents the amount of time that has passed since the first previous activation that has not yet been transmitted. The time offset value may be in 100 ms intervals i.e. 0=0 ms, 1=100 ms, 2=200 ms etc. It is possible to compress several of the above bytes into 4-bit upper and lower nibbles if the power budget requires it.

An alternative to the above-described sensors S will now be described.

A header on the dispenser's PCB may be available with power and an PC or similar interface for an embedded sensor which would be mounted directly to the dispenser's PCB. By having a communication interface directly to the dispenser's µC, the sensor may be able to transmit not only an activation event but also low battery level, cover opened, cover closed and IR obstruction events. Dispenser configuration information such as dose setting (1, 2, 3), IR range (long, short), battery level, etc. could also be transmitted at the request of a remote user. This information could be used to remotely monitor the health and configuration of a customer's dispenser. For example, the remote server could be configured, by a remote user, to generate a warning email that would automatically be sent to a customer with a list of individual dispensers that have low batteries allowing the customer to preempt dispenser failure.

The sensor may have more communication demands made of it than the first-described sensor, and therefore, will likely consume more power. An external power source may be necessary. This means that the sensor will only be used with the touch-free dispenser and use the dispenser's D-cell batteries as its power source.

The function of the hub H is to receive, time-date stamp and buffer activation data (event records) transmitted from the surrounding sensors within its range. It then passes this data along to the nearest hub or gateway when it is requested.

The hub H should preferably be able to receive transmitted data from sensors a minimum of 50 feet away in an indoor environment. Indoor range is a subjective term so it will be required to send data to a remote server. To do so, hubs that are out of the gateway's range will transmit and receive data from hubs that are within their range. In turn, these hubs will transmit and receive data from hubs within their range until the data finally reaches a gateway. This forwarding of data from one hub to another will form a simple ad hoc or mesh type of network. Each hub may be able to transmit to and receive data from other hubs or a gateway a minimum of 100 feet away in an indoor environment. The signal may pass through a maximum of two interior walls composed of drywall and metal studs. It will also be assumed that the signal may only pass through one exterior wall, firewall, or floor composed of formed concrete with embedded rebar.

External power may be required due to the large distance and communication demands placed on the hub. The hub may be powered from an external 6VDC to 12VDC source such as a class 2 transformer.

When activation event data is requested by the gateway, the hub will send the event record as in Table 3;

TABLE 3

| | | |
|---|---|---|
| Hub Device ID | = 0-255 | - 8-bit device ID to identify type of device (100 for the hub) |
| Hub Address Byte 0 | = 0-255 | - 32-bit (bytes 0 thru 3) hub address |
| Hub Address Byte 1 | = 0-255 | |
| Hub Address Byte 2 | = 0-255 | |
| Hub Address Byte 3 | = 0-255 | |
| Event Time Stamp Hours | = 0-23 | Hours time stamp applied when event record is received from sensor |
| Event Time Stamp Minutes | = 0-59 | Minutes time stamp applied when event record is received from sensor |
| Event Time Stamp Seconds | = 0-59 | Seconds time stamp applied when event record is received from sensor |
| Event Time Stamp Month | = 0-23 | Month time stamp applied when event record is received from sensor |
| Event Time Stamp Day | = 1-31 | Day time stamp applied when event record is received from sensor |
| Event Time Stamp Year | = 0-99 | Year time stamp applied when event record is received from sensor |
| Sensor Device ID | = 0-255 | 8-Bit Device ID to identify type of device |
| Sensor Address Byte 0 | = 0-255 | 32-Bit (bytes 0 thru 3) sensor address |
| Sensor Address Byte 1 | = 0-255 | |
| Sensor Address Byte 2 | = 0-255 | |
| Sensor Address Byte 3 | = 0-255 | |
| Sensor Event ID | = 0-255 | 8-bit event ID to identify type of event that occurred |
| Sensor Activation Count | = 0-255 | 8-bit count sensor activation count | assumed that the signal will only pass through a maximum of two interior walls composed of drywall and metal studs or that the signal will only pass through one exterior wall, firewall, or floor, composed of formed concrete with embedded rebar.

The hub H should preferably be able to process up to 100 sensors and up to 20 sensors transmitting activation events at the same time. A hub typically processes one event at a time so a maximum time-date stamp latency of 10 seconds may be used. This should allow enough time for each individual sensor event to be processed by the hub Each hub may be equipped with a battery backed real-time clock (RTC) with a minimum accuracy of +/−5 ppm. The gateway should attempt to update each hub's RTC at least once every 24 hours to keep all hubs synchronized. When a sensor's activation event is received, the hub will do the following: (1) log the event record; (2) log the current time of the RTC to create a time-date stamp for the event; (3) check the event record's time offset byte; (4) if time offset byte is not equal to 0, adjust time-date stamp accordingly; and (5) buffer event record with time-date stamp in circular queue. Some MSP430 µCs have a built-in RTC. This would eliminate the need for the hub to deal with time offset and keep things simple.

A circular queue may be used to buffer the last 10,000 activation events for all sensors within the hub's range. The queue will also serve as a local archive so that the remote server can request past events that may have been lost or corrupted. When the queue is full, new events will overwrite the oldest buffered events.

The hub may also function as a repeater. This wireless topology attempts to minimize the number of gateways The data in Table 3 may be in binary form using a proprietary protocol. This would make the data sufficiently difficult to decipher and eliminate the need for encryption. It is possible to compress the time-date stamp data but it is being presented in its current form to make parsing easier. Hub device ID, sensor event ID and sensor device ID may be included.

Hub installation is preferably as simple as possible. One should determine what sensors, hubs, or gateways are within range. An installer should preferably have a laptop PC available during installation. This will allow the use of a software tool that can be used to configure the hub (if necessary) and determine what devices are within range. The hub will have a half-duplex RS-485 serial port that will allow connection to the installer's PC.

The hub may be able to "discover" what other devices are within range without the need for the installer to intervene. This would be possible because each device will have a unique device ID and address combination. Discovery needs to occur within a reasonable amount of time because installers will charge by the hour.

The device may use a custom sheet metal enclosure or an ABS enclosure. Depending on size, mounting holes will be available in the PCB for fasteners. All connectors are preferably mounted at the PCB's edge for access through enclosure. Enclosure may be made of 1.5 mm steel or aluminum, with 2.50 mm from edge of PCB to outside surface of enclosure for connector placement. A right angle PCB mount SMA connector could be used so the antenna can be attached to the hub by the installer.

Although a preferred embodiment has been described, the invention is not limited to this embodiment and the scope of the invention is defined by the following claims.

Appendix A—Device Id Assignment

| Device | ID | Description |
|---|---|---|
| N/A | 0 | Broadcast to all device types |
| ProGiene G3 | 1 | ProGiene G3 touch-free group hand hygiene monitoring dispenser |
| ProSense Controller | 2 | ProSense touch-free faucet controller |
| RESERVED | 3 | Reserved for future use |
| ProGiene Data Logger | 4 | Hand held data logger for ProGiene G3 virtual network |
| Sensor T1 | 5 | Wireless sensor type 1 - contact closure event |
| Sensor T2 | 6 | Wireless sensors type 2 - multi-event with PC interface |
| Hub | 100 | Wireless hub/repeater |
| Gateway | 101 | Wireless gateway with embedded GSM modem |
| RESERVED | 250 | Reserved for future use |
| RESERVED | 251 | Reserved for future use |
| RESERVED | 252 | Reserved for future use |
| RESERVED | 253 | Reserved for future use |
| RESERVED | 254 | Reserved for future use |
| Master | 255 | Master device for master/slave RS-485 protocol |

Appendix B—Event Id Assignment

| Event | ID | Description |
|---|---|---|
| RESERVED | 0 | Reserved for future use |
| Dispenser Activation | 1 | Contact closure - dispenser activation |
| Dispenser Cover Opened | 2 | Dispenser's cover was opened |
| Dispenser Cover Closed | 3 | Dispenser's cover was closed |
| Object Blocking IR | 4 | Object placed under dispenser within IR range |
| Object Blocking IR Removed | 5 | Object under dispenser within IR range removed |
| RESERVED | 250 | Reserved for future use |
| RESERVED | 251 | Reserved for future use |
| RESERVED | 252 | Reserved for future use |
| RESERVED | 253 | Reserved for future use |
| RESERVED | 254 | Reserved for future use |
| RESERVED | 255 | Reserved for future use |

The invention claimed is:

1. A communication system for hygiene compliance monitoring comprising:
a plurality of hygiene monitoring sensors for collecting hygiene compliance data at a respective plurality of hygiene stations; and
a wireless link for transmitting the hygiene compliance data over a cellular telephone network to a central monitoring station, wherein the hygiene compliance data includes dispenser configuration information including dose setting and range setting of detectors.

2. The communication system according to claim 1, wherein the plurality of hygiene monitoring sensors transmit for hygiene compliance data to a central hub before transmission over the cellular telephone network.

3. The communication system according to claim 2, comprising a plurality of hubs which wirelessly communicate to a gateway before transmission over the cellular network.

4. The communication system according to claim 1, wherein the wireless link comprises a gateway which wirelessly receives the hygiene compliance data from a plurality of hygiene monitoring sensors before transmission over the cellular telephone network.

5. The communication system of claim 1, further including a remote server and database store at the central monitoring station.

6. The communication system of claim 5, further including an internet connection at the central station to enable internet access to the remote server and database store.

7. The communication system of claim 1, including a plurality of hubs, wherein at least one hub of the plurality can receive hygiene compliance data transmitted from another hub, and retransmit the data.

8. A communication system for hygiene compliance monitoring, comprising:
a plurality of hygiene monitoring sensors for collecting hygiene compliance data at a respective plurality of hygiene stations;
at least one hub which wirelessly receives hygiene compliance data transmitted from said plurality of hygiene monitoring stations;
a gateway which wirelessly receives hygiene compliance data transmitted from the hub; and
a wireless cellular telephone link for transmitting the hygiene compliance data from the gateway to a central monitoring station, wherein the hub includes automatic detection for detecting what hygiene sensors are within range to provide for automatic initialization and update of the system detectors in the system.

9. The communication system according to claim 8, comprising at least two hubs, each of which wirelessly receives hygiene compliance data from a different plurality of hygiene monitoring sensors.

10. The communication system according to claim 8, further including a remote server and database store at the central monitoring station.

11. The communication system of claim 10, further including an internet connection ant the central station to enable internet access to the remote server and database store.

12. The communication system of claim 8, including a plurality of hubs, wherein at least one hub of the plurality can receive hygiene compliance data transmitted from another hub, and retransmit the data.

13. A method for communicating hygiene compliance data, comprising:
collecting hygiene compliance data from a plurality of hygiene stations having monitoring sensors; and
transmitting the collected hygiene compliance data wirelessly over a cellular telephone network to a central monitoring station, wherein the hygiene compliance data includes dispenser configuration information including dose setting and range setting of detectors.

14. The method of claim 13, including the step of wirelessly transmitting the hygiene compliance data from the hygiene stations to a central hub, before transmitting the data wirelessly over the cellular network.

15. The method of claim 13, including using a gateway which wirelessly receives the hygiene compliance data from a plurality of hygiene monitoring sensors before transmission over the cellular telephone network.

16. The method of claim 13, including transmitting the data wirelessly over a plurality of hubs to a gateway before transmission over the cellular network.

17. The method of claim 13, including providing a remote server and database store at the central monitoring station.

18. The method of claim 13, including providing an Internet connection at the central station to enable internet access to the remote server and database store.

19. The method of claim 13, including providing a plurality of hubs, wherein at least one hub of the plurality receives the hygiene compliance data transmitted from another hub, and retransmits the data.

20. A communication system for hygiene compliance monitoring comprising:
a plurality of hygiene monitoring sensors for collecting hygiene compliance data at a respective plurality of hygiene stations; and
a wireless link for transmitting the hygiene compliance data over a cellular telephone network to a central monitoring station, wherein the hygiene compliance data includes dispenser status information including battery level and cover open/closed status.

21. A communication system for hygiene compliance monitoring comprising:
a plurality of hygiene monitoring sensors for collecting hygiene compliance data at a respective plurality of hygiene stations; and
a wireless link for transmitting the hygiene compliance data over a cellular telephone network to a central monitoring station, wherein the hygiene compliance data is stored in a circular queue in a local buffer, which is accessible by the central monitoring station to replace or correct lost or corrupt data.

22. A method for communicating hygiene compliance data, comprising:
collecting hygiene compliance data, from a plurality of hygiene stations having monitoring sensors; and
transmitting the collected hygiene compliance data wirelessly over a cellular telephone network to a central monitoring station, wherein the hygiene compliance data includes dispenser status information including battery level and cover open/closed status.

* * * * *